United States Patent [19]

Reichwein

[11] Patent Number: 4,866,385

[45] Date of Patent: Sep. 12, 1989

[54] CONSISTENCY MEASURING DEVICE

[75] Inventor: David P. Reichwein, Hershey, Pa.

[73] Assignee: Armstrong World Industries, Inc., Lancaster, Pa.

[21] Appl. No.: 217,180

[22] Filed: Jul. 11, 1988

[51] Int. Cl.⁴ .............................................. G01R 33/20
[52] U.S. Cl. ...................................... 324/300; 324/306
[58] Field of Search ............... 324/300, 306, 308, 309, 324/315, 316, 318, 224, 244, 248, 303, 307; 73/861.05, 861.08

[56] References Cited

U.S. PATENT DOCUMENTS

| | | | |
|---|---|---|---|
| 4,110,680 | 8/1978 | Bergmann | 324/306 |
| 4,531,093 | 7/1985 | Rollwitz | 324/300 |
| 4,638,251 | 1/1987 | King | 324/306 |
| 4,701,705 | 10/1987 | Rollwitz | 324/306 |

Primary Examiner—Michael J. Tokar

[57] ABSTRACT

An on-line method for consistency (percent solids by weight) testing of slurries. An aqueous slurry is piped through two stations, one of which is a nuclear magnetic resonance instrument and the other of which is a nuclear density (gamma radiation) gauge. The electrical signal outputs from the stations are processed by a computer to furnish a real time reading of consistency.

4 Claims, 1 Drawing Sheet

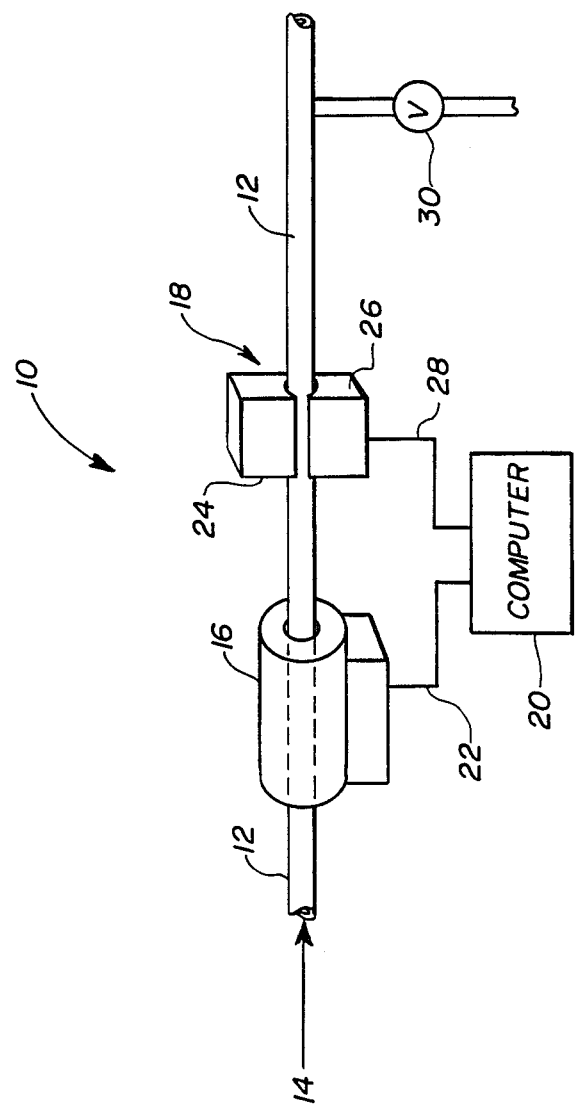

CONSISTENCY MEASURING DEVICE

SUMMARY OF THE INVENTION

This invention deals generally with testing of a liquid suspension of solids and, more specifically, with the consistency testing of slurries.

Virtually all methods of testing the consistency, the percent solids of a slurry, which are liquid solutions with solids suspended in them, involve either off-line hand-sampling techniques or shear-type transducers. Off-line hand-sampling is, by its very nature, an intermittent process which generally is unsatisfactory for meeting the process control needs of a high volume production process which can change between samples.

Sheer-type consistency transducers are limited in the range of consistencies they can measure and are effected by process parameters such as stock flow rate, air entrainment, formula variations, and abrasiveness. Currently there is no available on-line consistency measurement system that will give an accurate and absolute consistency measurement for stocks where the solids are abrasive.

The present invention solves these problems of on-line, real-time, measurement of slurry consistency and furnishes accurate, repeatable consistency measurement regardless of slurry air entrainment and formula variations.

This is accomplished by independently measuring the quantities of total slurry mass and liquid carrier mass and then using an on-line computer to combine the readings and provide a consistency measurement. A nuclear density gauge is used to measure the total slurry mass. Since nuclear density gauges using gamma radiation are currently used to measure mass, the key to the present invention is to accurately measure the mass of the liquid carrier. To measure the mass of the liquid carrier, a nuclear magnetic resonance instrument is used.

In basic terms, a nuclear magnetic resonance instrument operates by measuring the number of hydrogen atoms bonded to the molecules of the liquid carrier in the measuring field. This is done by passing the slurry through a high field strength magnet to temporarily disturb the hydrogen atom rotation, then the hydrogen atoms are bombarded by radio frequncy energy. When the radio frequency energy is cut off, the hydrogen atom relaxes and emits radio frequency energy of its own. The cumulative radio frequency field from the hydrogen atoms is detected by passing the slurry through a coil of wire that acts as an antenna. The radio frequency field strength detected by the antenna is related to the number of hydrogen atoms and therefore the mass of the carrier.

The nuclear magnetic resonance instrument is tuned to the carrier and therefore is not effected by entrapped air or solids with hydrogen bound atoms, and produces proportionately less signal when there is less liquid. The nuclear density gauge and the nuclear magnetic resonance instrument together provide all the data required for a consistency measurement. The nuclear magnetic resonance instrument measures the quantity of carrier bound hydrogen atoms, thus measuring the mass of the liquid carrier only, while the nuclear density gauge measures the total mass of the solids plus the liquid carrier passing through it.

These two measurements are then supplied to a computer which instantaneously calculates and displays consistency.

The method and apparatus described herein yield an on-line real-time consistency measurement independent of air entrainment and product formula variation.

BRIEF DESCRIPTION OF THE DRAWING

The FIGURE is a simplified block diagram of the preferred embodiment of the invention.

DETAILED DESCRIPTION OF THE INVENTION

The preferred embodiment of the invention is shown in the FIGURE in which consistency measuring apparatus 10 includes pipeline 12, through which flows slurry 14, and adjacent to which are installed nuclear magnetic resonance instrument 16 and nuclear density gauge 18.

Slurry 14 is a mixture of liquid and solids, a mixture in which the solids are largely insoluble and merely carried along by the liquid. Mud is generally considered a slurry, but much more valuable slurries are used in numerous industrial processes. While any liquid carrier can be used, water is probably the most common liquid carrier.

Since most industrial processes require close control of the constituents which make up a slurry, one particular measurement has become very important. It is consistency, which is the ratio, expressed in percent, of the weight of the solids in the slurry to the total weight of the slurry.

The present invention is capable of measuring the consistency of a slurry, and does so regardless of whether the liquid carrier has gas entrapped within it, because the invention independently measures the liquid weight rather than calculating the weight based on the assumption that all the volume which is not solid is liquid.

Moreover, the measurement range of the present invention far exceeds most measurement systems previously available because it measures the liquid quantity by a method which has no inherent saturation characteristic.

The present invention measures the liquid quantity with nuclear magnetic resonance instrument 16. As previously described, nuclear magnetic resonance instrument 16 actually measures the quantity of hydrogen bonded with other elements to form the liquid carrier in the system and therefore measures the weight of liquid carrier. It furnishes a simple, time varying, electrical signal to computer 20 by means of cable 22, and computer 20 converts the electrical signal into a weight based on previously programmed information.

The present invention does not make any claims in regard to nuclear magnetic resonance instruments. Such devices are well known and established in other fields. The most widely known of which is medical technology. In diagnostic medicine, nuclear magnetic resonance, also called magnetic resonance imaging or MRI, uses very high resolution equipment and elaborate display apparatus to visually display the function of human organs. While the present invention could make use of the elaborate medical instruments, it needs neither the high resolution, the elaborate display, nor the resolution between many materials.

Consistency testing apparatus 10 which needs to distinguish only the presence or absence of a single liquid material, requires only low resolution nuclear magnetic resonance instrument 16 and only a single output 22 of an electrical signal varying with time. Such a signal is available from the simplest nuclear magnetic resonance systems and generates an electrical signal which is related to the quantity of a specific substance, in this invention the liquid carrier, within the field of view. If the substance is flowing through the field of view, the electrical signal then varys according to variations in the quantity of material flowing past the pickup coil of instrument 16. Most important, if a bubble of air passes through the field of view, the quantity of liquid carrier is reduced and the electrical signal is reduced proportionally.

Nuclear magnetic resonance instrument 16 therefore furnishes the computer 20 an electrical signal which is always related to the weight of the liquid carrier, since it essentially measures the quantity of hydrogen passing through it.

With the liquid carrier weight accurately determined, it is only necessary to measure the total slurry weight in order to determine the consistency. The total slurry weight is measured by conventional nuclear density gauge 18. As is well established in the art, nuclear density gauge 18 uses cesium 137 source 24 to irradiate a section of pipeline 12 and ionization chamber 26 to measure the gamma radiation passing through pipeline 12. As the density of the total slurry varys the amount of radiation reaching ionization chamber 26 varys inversely, since more dense material causes more attenuation of the radiation. Nuclear density gauge 18 therefore furnishes an accurate measurement of the weight of slurry 14, the combined weight of the liquid carrier and the solids in slurry 14.

Nuclear density gauge 18 furnishes the information to computer 20 by means of cable 28, and computer 20, having available electrical signals related to the total weight of slurry 14 and the weight of one constituent, the liquid, of the two components of slurry 14, can easily be programmed to yield the percentage by weight of the other constituent, the solid materials.

Although the gamma ray attenuation measurement furnished by nuclear density gauge 18 and the hydrogen quantity measurement furnished by nuclear magnetic resonance instrument 16 could, along with the physical parameters of the materials, be used to calculate the consistency, a higher level of confidence in calibration is attained by relating the readings to empirical measurements. Therefore, sampling valve 30 is attached to pipeline 12. Thus, when consistency measuring apparatus 10 is first placed in operation or when different materials are first run in the system, a range of empirical measurements can be made by selecting samples and comparing them to the electrical signals available as they pass through the system. The use of empirical measurements is made easier by the fact that the relationship of the electrical signals to consistency is logarithmic. It is therefore only necessary to test a limited number of samples to secure an accurate calibration.

It is to be understood that the form of this invention as shown is merely a preferred embodiment. Various changes may be made in the function and arrangement of parts; equivalent means may be substituted for those illustrated and described; and certain features may be used independently from others without departing from the spirit and scope of the invention as defined in the following claims. For instance, slurries other than those with water as a liquid carrier could be measured.

What is claimed as new and for which Letters Patent of the United States are desired to be secured is:

1. A method of measuring the quantity of different materials in a slurry with at least two components therein, comprising the steps of:
   (a) measuring the presence of a specific material, which is one of the components of the slurry, within a first field of view of a nuclear magnetic resonance means which is tuned to the specific material and generates a signal related to the weight of specific material;
   (b) measuring the slurry within a second field of view adjacent the first field of view so that a nuclear density means generates a signal related to the weight of the slurry in the second field of view; and
   (c) comparing the signal on the weight of specific material to the signal on the weight of the slurry to calculate the consistency of the slurry which is the percent solids of the slurry.

2. A method of measuring the quantity of different materials in a slurry as set forth in claim 1, comprising the steps of:
   (a) the specific material being measured by the nuclear magnetic resonance means is water; and
   (b) the slurry is a mixture of largely insoluble solids carried along by the liquid.

3. A method of measuring the quantity of different materials in a slurry as set forth in claim 2, comprising the steps of:
   (a) feeding the two signals generated to a computer means to subtract the weight of liquid from the weight of the slurry to calculate the weight of the solids and then divide the weight of solids by the weight of slurry to determine the consistency of the slurry.

4. A method of measuring the quantity of different materials in a slurry as set forth in claim 3, comprising the steps of:
   (a) said slurry has gas entrapped therein,
   (b) said gas presence reduces the signal from the nuclear magnetic resonance means and the nuclear density means so that consistency can still be accurately calculated.

* * * * *